United States Patent [19]

Cullen et al.

[11] Patent Number: 4,996,361

[45] Date of Patent: Feb. 26, 1991

[54] PROCESS FOR THE PREPARATION OF OPTICALLY ACTIVE SECONDARY ARYLAMINES

[75] Inventors: William R. Cullen, Vancouver, Canada; Michael D. Fryzuk, Kaiserslautern, Fed. Rep. of Germany; Brian R. James, Vancouver, Canada; Guo-Jun Kang, Vancouver, Canada; James P. Kutney, Vancouver, Canada; Roberto Spogliarich, Trieste, Italy; Ian S. Thorburn, Vancouver, Canada

[73] Assignee: The University of British Columbia, Vancouver, Canada

[21] Appl. No.: 79,625

[22] Filed: Jul. 30, 1987

[51] Int. Cl.$^5$ ............................................. C07C 57/00
[52] U.S. Cl. .................................. 564/304; 564/302; 568/13
[58] Field of Search ....................... 564/301, 302, 304; 568/13

[56] References Cited

U.S. PATENT DOCUMENTS

| | | | |
|---|---|---|---|
| 2,608,583 | 8/1952 | Aschner | 564/302 |
| 3,968,147 | 7/1976 | Solodar | 564/304 X |
| 4,115,417 | 9/1978 | Valentine, Jr. | 568/8 X |
| 4,187,313 | 2/1980 | Gschwend et al. | 564/304 X |
| 4,440,936 | 4/1984 | Riley | 564/192 X |
| 4,556,740 | 12/1985 | Hansen et al. | 568/13 |
| 4,613,460 | 9/1986 | Casati et al. | 560/41 |
| 4,658,060 | 4/1987 | Gold et al. | 564/304 X |

FOREIGN PATENT DOCUMENTS 0104375 4/1984 European Pat. Off.

OTHER PUBLICATIONS

Kagan et al, Journal of Organometallic Chemistry, vol. 9 (1975), pp. 353–365.
Levi et al, J.C.S. Chem. Comm. (1975), pp. 6 & 7.
Kumada et al, Chemical Abstracts, vol. 90 (1979) 121760q.
Vastag et al, Chemical Abstracts, vol. 87 (1977), 152370e.
Kang et al, J. Chem. Soc., Chem. Commun., 1988, pp. 1466 & 1467.
H. B. Kagan, Chiral Ligands for Asymmetric Catalysis, Asymmetric Synthesis, vol. 5, pp. 13–23 (1985).
M. Green et al., J. Chem. Soc. (A), pp. 2334 (1971).
Sandor Vastag et al., Journal of Molecular Catalysis, 22 (1984) 283–287.

Primary Examiner—Robert V. Hines
Attorney, Agent, or Firm—Kevin T. Mansfield

[57] ABSTRACT

Asymmetric hydrogenation of prochiral N-arylketimines to give optically active secondary amines at a temperature from −40° to 80° C., under a hydrogen pressure of $10^6$ to $10^8$ Pa and with the addition of catalytic amounts of a rhodium compound of the formula III or IIIa $$[XRhYZ] \quad \text{(III)}$$
$$\text{or}$$
$$[XRhY]^{\oplus}A^{\ominus} \quad \text{(IIIa)}$$

in which X is 2 olefin ligands or a diene ligand, Y is a chiral diphosphine in which the secondary phosphine groups are linked by 2–4 C atoms and which, together with the Rh atom, forms a 5-membered, 6-membered or 7-membered ring, or Y is a chiral disphosphinite in which the phosphinite groups are linked via 2 C atoms and which, together with the Rh atom, forms a 7-membered ring, Z is Cl, Br or I and A$^-$ is the anion of an oxygen acid or complex acid.

12 Claims, No Drawings

PROCESS FOR THE PREPARATION OF OPTICALLY ACTIVE SECONDARY ARYLAMINES

The present invention relates to a process for the preparation of optically active secondary amines by asymmetrical hydrogenation of prochiral N-arylketimines by means of chiral rhodium diphosphine or diphosphinite complexes.

EP-A 0,104,375 describes chiral diphosphine ligands, the complexes of which with metals of group VIII of the periodic system can be used as catalysts in the asymmetrical hydrogenation of α-(acylamino)-acrylic acids.

S. Vastag et al. describe, in the J. of Molecular Catalysis, 22, pp. 283–287 (1984), the asymmetrical hydrogenation of prochiral N-benzylketimines using rhodium complexes containing chiral diphosphine ligands. The chemical conversion and the reproducibility of the optical yields are low.

It has been found that rhodium compounds containing chiral diphosphine or diphosphinite ligands are particularly suitable homogeneous, asymmetrical catalysts for the hydrogenation of prochiral N-arylketimines. Increased and reproducible optical yields of optically active secondary N-arylamines are achieved under mild reaction conditions and with high chemical conversions. Optically active means an excess of one enantiomer having the R-configuration or S-configuration.

The present invention relates to a process for the preparation of optically active secondary N-arylamines of the formula I

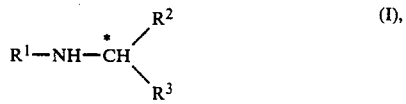

in which $R^1$ is $C_6$–$C_{12}$-aryl or $C_4$–$C_{11}$-heteroaryl which is attached via a ring C atom and contains 1 or 2 ring hetero atoms which can be substituted by $C_1$–$C_{12}$-alkyl, $C_1$–$C_{12}$-alkoxy, $C_1$–$C_{12}$-alkylthio, $C_1$–$C_6$-halogenoalkyl, halogen, —OH, —CN, $C_6$–$C_{12}$-aryl, $C_6$–$C_{12}$-aryloxy, $C_6$–$C_{12}$-arylthio or $C_7$–$C_{16}$-aralkyl, $C_7$–$C_{16}$-aralkoxy or $C_7$–$C_{16}$-aralkylthio, the aryl moieties of which radicals in turn may be substituted by $C_1$–$C_4$-alkyl, $C_1$–$C$ -alkoxy, $C_1$–$C_4$-alkylthio, halogen, —OH, —CN, —CONR$^4$R$^5$ or —COOR$^4$, or by secondary amino having 2 to 24 C atoms,

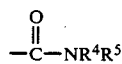

or —COOR$^4$, R$^4$ and R$^5$ independently of one another being $C_1$–$C_{12}$-alkyl, phenyl or benzyl or R$^4$ and R$^5$ together being tetramethylene or pentamethylene or 3-oxapentylene; R$^2$ and R$^3$ are different from one another and are $C_1$–$C_{12}$-alkyl or cycloalkyl having 3-8 ring C atoms which are unsubstituted or substituted by —OH, —CN, halogen, $C_1$–$C_{12}$-alkoxy, phenoxy, benzyloxy, secondary amino having 2 to 24 C atoms,

or —COOR$^4$, or are $C_6$–$C_{12}$-aryl or $C_7$–$C_{16}$-aralkyl which are unsubstituted or substituted like R$^1$, or are or —COOR$^4$R$^5$ or —COOR$^4$ in which R$^4$ and R$^5$ are as defined above; or R$^1$ is as defined above and R$^2$ and R$^3$ together are alkylene which has 2 to 5 C atoms and can be interrupted by 1 or 2 —O—, —S— or —NR$^4$- groups and/or can be substituted by =O or substituted as above for R$^2$ and R$^3$ when they are alkyl, and/or is fused with benzene, furan, thiophene or pyrrole, or R$^2$ is as defined above and R$^3$ is alkylene which has 2 to 5 C atoms and is attached to R$^1$ and can be interrupted by 1 or 2 —O—, —S— or —NR$^4$- groups, and/or can be substituted by =O L or substituted as above for R$^2$ and R$^3$ when they are alkyl, and/or is fused with benzene, furan, thiophene or pyrrole, and * means predominantly the R-configuration or S-configuration, by asymmetrically catalyzed hydrogenation of N-arylated, prochiral ketimines of the formula II

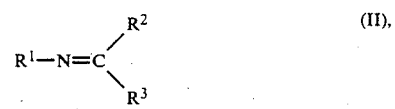

in which $R^1$, $R^2$ and $R^3$ are as defined above, in the presence of complex salts of a noble metal containing chiral ligands, which comprises carrying out the hydrogenation at a temperature from −40 to 80° C. and under a hydrogen pressure of $10^6$ Pa to $10^8$ Pa and adding to the reaction mixture catalytic amounts of a rhodium compound of the formula III or IIIa

in which X is two olefin ligands or one diene ligand, Y is a chiral diphosphine in which the secondary phosphine groups are linked by 2–4 C atoms and which, together with the Rh atom, forms a 5-membered, 6-membered or 7-membered ring, or Y is a chiral diphosphinite in which the phosphinite groups are linked via 2 C atoms and which, together with the Rh atom, forms a 7-membered ring, Z is Cl, Br or I and A ⊖ is the anion of an oxygen acid or complex acid.

R$^1$ can be substituted in any desired positions by identical or different radicals, for example by 1 to 5, preferably 1 to 3, substituents. Substitution in the two ortho-positions relative to the N atom can have a favourable effect on the desired yields, R$^2$ in this case being preferably not aryl. Preferably, both ortho-positions are substituted, in particular by $C_1$–$C_{12}$-alkyl.

The following are suitable substituents for R$^1$ and also R$_2$ and R$_3$ when they are aryl and aralkyl: $C_1$–$C_{12}$-alkyl, $C_1$–$C_{12}$-alkoxy or $C_1$–$C_{12}$-alkylthio, preferably $C_1$–$C_6$-alkyl, $C_1$–$C_6$-alkoxy or $C_1$–$C_6$-alkylthio and particularly $C_1$–$C_4$-alkyl, $C_1$–$C_4$-alkoxy or $C_1$–$C_4$-alkylthio, for example methyl, ethyl, propyl, n-, i- and t-butyl, the isomers of pentyl, hexyl, octyl, nonyl, decyl, undecyl and dodecyl, and also corresponding alkoxy and alkylthio radicals; $C_1$–$C_6$-halogenoalkyl, preferably $C_1$–$C_4$-halogenoalkyl, preferably having F and Cl as the halogen, for example trifluoromethyl, trichloromethyl, difluorochloromethyl, fluorodichloromethyl, 1,1-difluoroeth-1-yl, 1,1-dichloroeth-1-yl, 1,1,1,-trichloroeth-2-yl, 1,1,1-trifluoroeth-2-yl, pentachloroethyl, pentafluoroethyl, 1,1,1-trifluoro-2,2dichloroethyl, n-perfluoropropyl, i-perfluoropropyl, n-perfluorobutyl, fluoromethyl, chloromethyl, difluoromethyl, dichloromethyl, 1-fluoroeth-2-yl, 1- chloroeth-2-yl, 1-fluoroeth-1-yl, 1-chloroeth-1-yl, 1-, 2- or 3-fluoro-prop1-yl or -prop-2-yl or -prop-3-yl, 1-, 2- or 3-chloro-prop-1-yl or -prop-2-yl or -prop-3-yl, 1-fluoro-but-1-yl, -but-2-yl, -but-3-yl or -but-4-yl, 1-chloro-but-1-yl, -but-2-yl, -but-3-yl or -but-4-yl, 2,3-dichloroprop-1-yl, 1-chloro-2-fluoroprop-3-yl or 2,3-dichlorobut-1-yl; halogen, preferably F and Cl; $C_6$–$C_{12}$-aryl, $C_6$–$C_{12}$-aryloxy or $C_6$–$C_{12}$-arylthio in which aryl is preferably naphthyl and especially phenyl, $C_7$–$C_{16}$-aralkyl, $C_7$–$C_{16}$-aralkoxy and $C_7$–$C_{16}$-aralkylthio in which the aryl radical is preferably naphthyl and especially phenyl and the alkylene radical is linear or branched and contains 1 to 10, preferably 1 to 6, and particularly 1–3, C atoms, for example benzyl, naphthylmethyl, 1-phenyleth-1-yl, 1-phenyleth-2-yl, 2-phenyleth-1-yl or 2-phenyleth-2-yl, or 1-, 2- or 3-phenylprop-1-yl, 1-, 2- or 3-phenylprop-2-yl or 1-, 2- or 3-phenylprop-3-yl, benzyl being particularly preferred; the radicals previously mentioned containing aryl groups can in turn be monosubstituted or polysubstituted, for example by $C_1$–$C_4$-alkyl, $C_1$–$C_4$-alkoxy, $C_1$–$C_4$-alkylthio, halogen, —OH, —CN, —CONR$^4$R$^5$ or —COOR$^4$, R$^4$ and R$^5$ being defined as above; examples are methyl, ethyl, n-propyl, ipropyl, butyl, corresponding alkoxy and alkylthio radicals, F, Cl, Br, dimethylcarbamoyl, methylethylcarbamoyl, diethylcarbamoyl and methoxy carbonyl, ethoxycarbonyl, phenoxycarbonyl, benzyloxycarbonyl, secondary amino having 2 to 24, preferably 2 to 12 and especially 2 to 6, C atoms, the secondary amino preferably containing 2 alkyl groups, for example dimethylamino, methylethylamino, diethylamino, methylpropylmethyl-n-butylamino, di-n-propylamino, di-n-butylamino and di-n-hexylamino; —CONR$^4$R$^5$ in which R$^4$ and R$^5$ independently of one another are $C_1$–$C_{12}$-alkyl, preferably $C_1$–$C_6$-alkyl and especially $C_1$–$C_4$-alkyl, or R$^4$ and R$^5$ together are tetramethylene or pentamethylene or 3-oxapentylene, it being possible for the alkyl to be linear or branched, for example dimethylcarbamoyl, methylethylcarbamoyl, diethylcarbamoyl, methyl-n-propylcarbamoyl, ethyl-n-propylcarbamoyl, di-n-propylcarbamoyl, methyl-n-butylcarbamoyl, ethyl-n-butylcarbamoyl, n-propyl-n-butylcarbamoyl and di-n-butylcarbamoyl; —COOR$^4$ in which R$^4$ is $C_1$–$C_{12}$-alkyl, preferably $C_1$–$C_6$-alkyl, which can be linear or branched, ethyl, n-propyl, i-propyl, n-, i- and t-butyl and the isomers of pentyl, hexyl, heptyl, octyl, nonyl, decyl, undecyl and dodecyl.

As aryl, R$^1$ is preferably unsubstituted or substituted naphtyl and especially phenyl. As heteroaryl, R$^1$ is preferably a 5-membered or 6-membered ring which has 1 or 2 identical or different hetero atoms, especially O, S or N, and preferably contains 4 or 5 C atoms and can be condensed with benzene. Examples of heteroaromatic structures from which R$^1$ can be derived are furan, pyrrole, thiophene, pyridine, pyrimidine, indole and quinoline.

The same preferences apply to the substituents of R$^2$ and R$^3$ as for the substituents of R$^1$. As alkyl, R$^2$ and R$^3$ are preferably unsubstituted or substituted $C_1$–$C_6$-alkyl, especially $C_1$–$C_4$-alkyl, which can be linear or branched. Examples are methyl, ethyl, i-propyl, n-propyl, i-, n- and t-butyl and the isomers of pentyl, hexyl, heptyl, octyl, nonyl, decyl undecyl and dodecyl.

As unsubstituted or substituted cycloalkyl, R$^2$ and R$^3$ preferably contain 3 to 6, especially 5 or 6, ring C atoms. Examples are cyclopropyl, cyclobutyl, cyclopentyl, cyclohexyl, cycloheptyl and cyclooctyl.

As aryl, R$^2$ and R$^3$ are preferably unsubstituted or substituted naphthyl and especially phenyl. As aralkyl, R$^2$ and R$^3$ are preferably unsubstituted or substituted phenyl-alkyl having 1–10, preferably 1 to 6 and especially 1 to 4, C atoms in the alkylene, it being possible for the alkylene to be linear or branched. Examples are especially benzyl, and also 1-phenyleth-1-yl, 2-phenyleth-1-yl, 1-phenyl-prop-1-yl, 1-phenylprop-2-yl, 1-phenylprop-3-yl, 2-phenylprop-1-yl, 2-phenylprop-2yl and 1-phenylbut-4-yl.

In R$^2$ and R$^3$ as —CONR$^4$R$^5$ and —COOR$^4$, R$^4$ and R$^5$ are preferably $C_1$–$C_6$-alkyl, especially $C_1$–$C_4$-alkyl, or R$^4$ and R$^5$ together are tetramethylene, pentamethylene or 3-oxapentylene. Examples of alkyl have been mentioned previously.

As alkylene, R$^2$ and R$^3$ together or R$^3$ attached to R$^1$ are preferably interrupted by 1 —O—, —S— or —NR$^4$-, preferably —O—. Together with the C atom or with the -N=C group to which they are attached, R$^2$ and R$^3$ together or R$^3$ attached to R$^1$ preferably form a 5-membered or 6-membered ring. The preferences mentioned previously apply to the substituents. As fused alkylene, R$^2$ and R$^3$ together or R$^3$ attached to R$^1$ are preferably alkylene which is fused with benzene or pyridine. The following are examples of alkylene: ethylene, 1,2-propylene, 1,3-propylene, 1,2-, 1,3- or 1,4-butylene, 1,5-pentylene and 1,6-hexylene. The following are examples of alkylene which is interrupted or substituted by =O: 2-oxa-1,3-propylene, 2-oxa-1,4-butylene, 2-oxa-1,5-pentylene, 3-oxa-1,5-pentylene, 3-thia-1,5-pentylene, 2-thia-1,4-butylene, 2-thia-1,3-propylene, 2-methylimino-1,3-propylene, 2-ethylimino-1,4-butylene, 2-methylimino-1,5-pentylene, 3-methylimino-1,5-pentylene, 1-oxo-2-oxa-1,3-propylene, 1-oxo-2-oxa-1,4-butylene, 2-oxo-3-oxa-1,4-butylene, 1-oxa-2-oxo-1,5-pentylene. The following are examples of alkylene which is fused or attached to R$^1$:

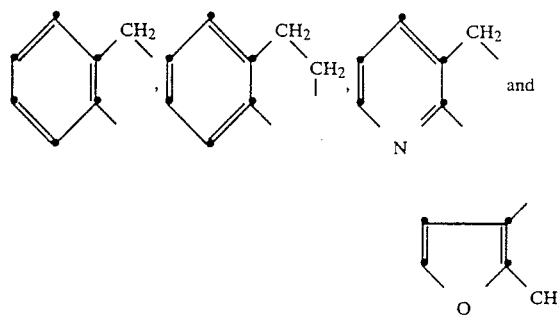

The following are examples of alkylene which is fused or attached to R$^1$ and interrupted and, if appropriate, substituted by an =O

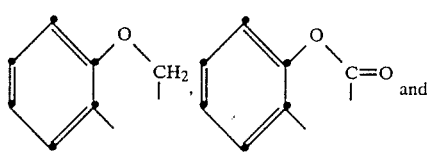

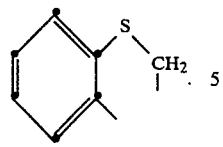

In a preferred group, $R^1$ in formula II is 2,6-dimethylphen-1-yl or 2-methyl-6-ethylphen-1-yl, $R^2$ and $R^3$ is methoxymethyl.

N-Arylimines of the formula II are known or can be prepared by known processes from ketones and arylamines. In one embodiment of the process, the N-arylimines of the formula II can also be prepared in situ from the corresponding ketones and arylamines.

The process is preferably carried out at a temperature from −20 to 50° C., especially −20 to 20° C. and particularly −20 to 10° C., and preferably under a hydrogen pressure of $4\times10^6$ to $5\times10^7$ Pa, especially $7\times10^6$ to $3\times10^7$ Pa.

As the olefine ligand in the formulae III and IIIa, X can be, for example, butene, propene and especially ethylene, and the diene ligand is preferably an open-chain or cyclic diene in which the diene groups are attached by means of one or two C atoms. The diene is preferably hexadiene, cyclooctadiene or especially norbornadiene.

In the chiral diphosphine, the phosphine groups are preferably attached via an aliphatic group which has 2–4 C atoms and can be substituted by $C_1$–$C_4$-alkyl, $C_5$-cycloalkyl, $C_6$-cycloalkyl, phenyl or benzyl. The aliphatic group can be alkylene or a cycloaliphatic group having 5 or 6 ring C atoms or an aliphatic-heterocyclic group having 1 to 2 —O— or =N-$C_1$-$C_{12}$-alkyl, =N-$C_1$-$C_{12}$-acyl, =N-$C_1$-$C_{12}$-amino-carbonyl, phenyl or benzyl groups and 3–5 C atoms in the ring. The rings can be substituted by $C_1$–$C_4$-alkyl, $C_5$–$C_7$-cycloalkyl, phenyl, or benzyl.

In the formulae III or IIIa, Y is preferably a chiral diphosphine in which the phosphine groups are linked by means of 2 C atoms and which, together with the Rh atom, forms a 5-membered ring.

The phosphine groups and phosphinite groups preferably contain $C_1$–$C_{12}$-alkyl, cycloalkyl which has 5 to 8 ring C atoms and which can be substituted by 1 to 3 $C_1$–$C_6$alkyl groups, phenyl, $C_7$–$C_{12}$-phenylalkyl or alkylphenyl-alkyl having 1 to 6 C atoms in the alkyl groups and 1 to 5 C atoms in the alkylene group. t-Butyl, phenyl, benzyl or cyclohexyl are particularly preferred. Suitable chiral diphosphines are described in H. B. Kagan, Chiral Ligands for Asymmetric Catalysis, Asymmetric Synthesis, Volume 5, pp. 13–23, Academic Press, Inc., N.Y. (1985).

The following are examples (Ph is phenyl):

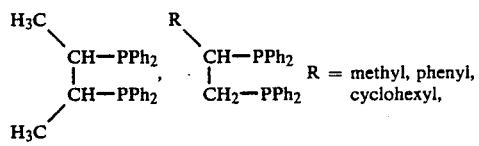

R = methyl, phenyl, cyclohexyl,

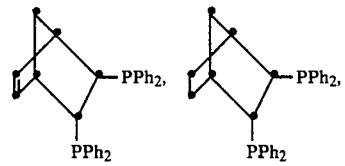

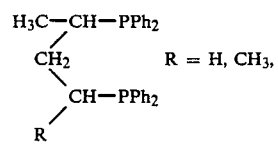
R = H, $CH_3$,

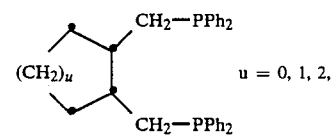
u = 0, 1, 2,

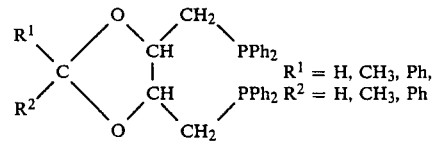
$R^1$ = H, $CH_3$, Ph,
$R^2$ = H, $CH_3$, Ph

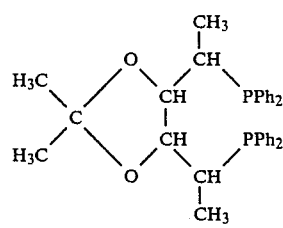

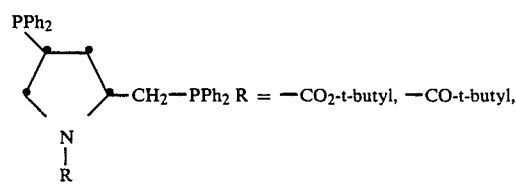
R = $-CO_2$-t-butyl, $-CO$-t-butyl, $-CONHC_1$-$C_4$-alkyl,

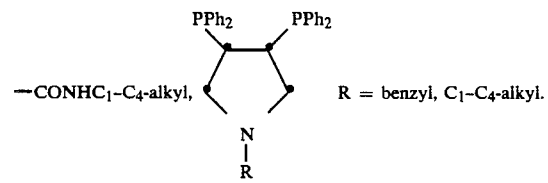
R = benzyl, $C_1$-$C_4$-alkyl.

An example of diphosphinites is 1-0-phenyl-4,6-0-(R)-benzylidene-2,3-0-bis-(diphenylphosphino)-β-D-glucopyranoside of the formula

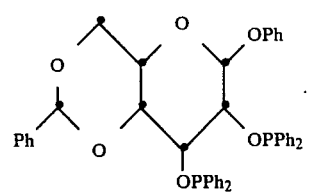

In formula III, Z is preferably Cl or Br. In formula IIIa, A⊖ is preferably $ClO_4\ominus$, $CF_3SO_3\ominus$, $BF_4\ominus$, $B(Phenyl)_4\ominus$, $PF_6\ominus$, $SbCl_6\ominus$, $AsF_6\ominus$ or $SbF_6\ominus$.

A preferred group of rhodium compounds comprises those of the formula III in which X is norbornadiene, Z is Cl and Y is (R)— or (S)—

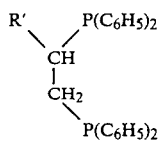

in which R' is methyl, phenyl or cyclohexyl.

The rhodium compounds of the formulae III and IIIa are known or can be prepared by known processes, see, for example, M. Green et al., J. Chem. Soc. (A), pp. 2334 et seq. (1971).

The rhodium compounds can be employed in the form of compounds which have been isolated. It is advantageous to prepare the compounds in situ and to use them without further treatment. The rhodium compounds are preferably employed in amounts of 0.01 to 5, especially 0.05 to 2, mol %, relative to the compounds of the formula II. The molar ratio of the compound of the formula II to the compound of the formula III or IIIa can be 1000 to 20, preferably 200 to 50.

The reaction can be carried out in the absence or in the presence of solvents. The following are examples of suitable solvents which can be employed on their own or as a mixture of solvents: aliphatic and aromatic hydrocarbons, for example pentane, hexane, cyclohexane, methylcyclohexane, benzene, toluene and xylene; alcohols, for example methanol, ethanol, propanol and butanol; ethers, for example diethyl ether, diethylene glycoldimethyl ether, tetrahydrofuran and dioxane; halogenated hydrocarbons, for example methylene chloride, chloroform, 1,1,2,2-tetrachloroethane and chlorobenzene; esters and lactones, for example ethyl acetate, butyrolactone and valerolactone; and acid amides and lactams, for example dimethylformamide, dimethylacetamide and N-methylpyrrolidone. It is preferable to use mixtures of alcohols and aromatic hydrocarbons, for example methanol/benzene or methanol/toluene.

The compounds of the formula I are biologically active substances or intermediates for the preparation of such substances containing an N-aryl secondary amine group, particularly in the field of pharmaceuticals and agricultural chemicals. Thus, for example, o,o-dialkylaryl ketamine derivatives, particularly those containing alkyl and/or alkoxyalkyl groups, have a fungicidal action, especially a herbicidal action. The derivatives can be amine salts, acid amides, for example amides of chloroacetic acid, tertiary amines and ammonium salts (see, for example EP-A 0,077,755 and EP-A 0,115,470).

The following examples illustrate the invention in greater detail.

EXAMPLE 1

N-(2,6-dimethylphen-1-yl)-methoxymethyl methyl ketimine is introduced, under $N_2$ as a protective gas, into a 250 ml two-necked flask. The flask is evacuated to $5 \times 10^3$ Pa and is flushed with nitrogen. The solvent is then added and the mixture is stirred for 2 minutes at room temperature (solution A). '1 The solvent is introduced, under $N_2$ as a protective gas, into a 50 ml two-necked flask. [Rh(Norbornadiene)Cl]$_2$ and chiral diphosphine are then added successively. After each addition the mixture is stirred until a homogeneous solution is present (solution B).

The solutions A and B are introduced successively by means of a capillary and with exclusion of air into a 0.3 l steel autoclave. $6.9 \times 10^6$ Pa of hydrogen are injected through a gas inlet valve. The temperature is 20° C. The reaction is carried out under a constant hydrogen pressure of $6.9 \times 10^6$ Pa until no further absorption of hydrogen takes place. The reaction mixture is then flushed by means of nitrogen into a 250 ml flask.

The solvent is removed at 80° C. on a rotary evaporator. The crude product obtained is distilled in a high vacuum (1–10 Pa). The chemical yield is then determined by means of gas chromatography (OV-101 capillary column). The optical yield is determined by comparison with the value of $[\alpha] 20/365 = -124.3°$ (C=3, hexane) obtained for the optically pure secondary amine. Further data can be seen in Table 1 below.

TABLE 1

| Reaction with various chiral diphosphines (Ph = phenyl) | | | | |
|---|---|---|---|---|
| Chiral diphosphine | Substrate: catalyst molar ratio | Reaction time (hours) | Chemical yield (%) | Optical yield (% ee) |
| (α-POOP) | 50 | 192 | 73 | 7.8 |
| (DIOP) | 50 | 42 | 18 | 8.0 |

TABLE 1-continued

Reaction with various chiral diphosphines
(Ph = phenyl)

| Chiral diphosphine | Substrate: catalyst molar ratio | Reaction time (hours) | Chemical yield (%) | Optical yield (% ee) |
| --- | --- | --- | --- | --- |
|  (PHENPHOS) | 50 | 18 | 83 | 21.2 |
| 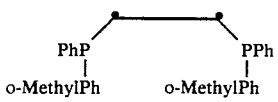 (DIPAMP) | 100 | 44 | 50 | 25.3 |
|  (CHIRAPHOS) | 50 | 66 | 88 | 37.8 |
|  (PROPHOS) | 100 | 18 | 91 | 39.6 |
| 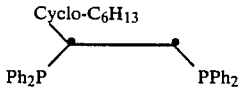 (CYCPHOS) | 100 | 44 | 99 | 52.8 |
| 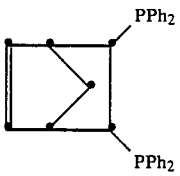 (NORPHOS) | 100 | 48 | 99 | 51.5 |

Reaction conditions 0.1 mmol of catalyst (prepared in situ from 0.05 mmol of [Rh(norbornadiene)Cl]$_2$ and 0.1 mmol of chiral diphosphine or diphosphinite); solvent: 10 ml of a 1:1 mixture of methanol and benzene; temperature 20° C.; hydrogen pressure: $6.9 \times 10^6$ Pa.

EXAMPLE 2

The process is as in Example 1, and the reaction is carried out at various temperatures. The substrate to catalyst ratio is 100. The pressure is $10.34 \times 10^6$ Pa. The solvent in the first two reactions in Table 2 is 10 ml of 1:1 methanol/benzene, in other cases 15 ml of 2:1 methanol/toluene.

TABLE 2

| Chiral diphosphine | Reaction temperature (0° C.) | Reaction time (hours) | Chemical yield (%) | Optical yield (% ee) |
| --- | --- | --- | --- | --- |
| NORPHOS | 5 | 68 | 100 | 59.5 |
| CYCPHOS | 4 | 66 | 100 | 60.2 |
| NORPHOS | −10 | 68 | 100 | 64.0 |
| CYCPHOS | −10 | 20 | 100 | 68.8 |
| CYCPHOS | −25 | 70 | 100 | 73.0 |

EXAMPLE 3

The process is as in Example 1 and CYCPHOS is used as the chiral diphosphine. The reaction is carried out in 15 ml of 2:1 methanol/toluene at −10° C. and under a hydrogen pressure of $10.34 \times 10^6$ Pa, using various substrate: catalyst ratios. The results are shown in Table 3.

TABLE 3

| Substrate: catalyst molar ratio | Reaction time (hours) | Chemical yield (%) | Optical yield (% ee) |
| --- | --- | --- | --- |
| 1:200 | 24 | 31 | 68.8 |
| 1:500 | 66 | 81 | 68.2 |

TABLE 3-continued

| Substrate: catalyst molar ratio | Reaction time (hours) | Chemical yield (%) | Optical yield (% ee) |
|---|---|---|---|
| 1:1000 | 168 | 67 | 69.2 |

What is claimed is:

1. A process for the preparation of optically active secondary N-arylamines of the formula I

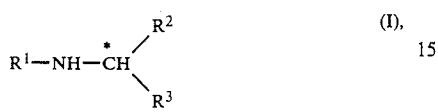

in which $R^1$ is $C_6$–$C_{12}$-aryl or $C_4$–$C_{11}$-heteroaryl which is attached via a ring C atom and contains 1 to 2 ring hetero atoms which can be substituted by $C_1$–$C_{12}$-alkyl, $C_1$–$C_{12}$-alkoxy, $C_1$–$C_{12}$-alkylthio, $C_1$–$C_6$-halogenoalkyl, halogen, —OH, —CN, $C_6$–$C_{12}$-aryl, $C_6$–$C_{12}$-aryloxy, $C_6$–$C_{12}$-arylthio or $C_7$–$C_{16}$-aralkyl, $C_7$–$C_{16}$-aralkoxy or $C_7$–$C_{16}$-aralkylthio, the aryl moieties of which radicals in turn may be substituted by $C_1$–$C_4$-alkyl, $C_1$–$C_4$-alkoxy, $C_1$–$C_4$-alkylthio, halogen, —OH, —CN, —CONR$^4$R$^5$ or —COOR$^4$, or by secondary amino having 2 to 24 C atoms,

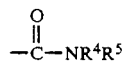

or —COOR$^4$, R$^4$ and R$^5$ independently of one another being $C_1$–$C_{12}$-alkyl, phenyl or benzyl or R$^4$ and R$^5$ together being tetramethylene or pentamethylene or 3-oxapentylene; R$^2$ and R$^3$ are different from one another and are $C_1$–$C_{12}$-alkyl or cycloalkyl having 3–8 ring C atoms which are unsubstituted or substituted by —OH, —CN, halogen, $C_1$–$C_{12}$-alkoxy, phenoxy, benzyloxy, secondary amino having 2 to 24 C atoms,

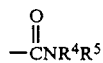

or —COOR$^4$, or are $C_6$–$C_{12}$-aryl or $C_7$–$C_{16}$-aralykl which are unsubstituted or substituted like R$^1$, or are or —CONR$^4$R$^5$ or —COOR$^4$ in which R$^4$ and R$^5$ are as defined above; or R$_1$ is as defined above and R$^2$ and R$^3$ together are alkylene which has 2 to 5 C atoms and which can be interrupted by 1 or 2 —O—, —S— or —NR$^4$- groups and/or can be submitted by =O or substituted as above for R$^2$ and R$^3$ when they are alkyl, and/or is fused with benzene, furan, thiophene or pyrrole, or R$^2$ is as defined above and R$^3$ is alkylene which has 2 to 5 C atoms and is attached to R$^1$ and can be interrupted by 1 or 2 —O—, —S— or -NR$^4$- groups, and/or can be substituted by =O or substituted as above for R$^2$ and R$^3$ when they are alkyl, and/or is fused with benzene, furan, thiophene or pyrrole, and * means predominantly the R-configuration or S-configuration, by asymmetrically catalyzed hydrogenation of N-arylated, prochiral ketimines of the formula II

in which $R^1$, $R^2$ and $R^3$ are as defined above, in the presence of complex salts of a noble metal containing chiral ligands, which comprises carrying out the hydrogenation at a temperature from −40 to 80° C. and under hydrogen pressure of $10^6$ Pa to $10^8$ Pa and adding to the reaction mixture catalytic amounts of a rhodium compound of the formula III or IIIa

in which X is two olefin ligands or one diene ligand, Y is a chiral diphosphine in which the secondary phosphine groups are linked by 2–4 C atoms and which, together with the Rh atom, forms a 5-membered, 6-membered or 7-membered ring, or Y is a chiral disphosphinite in which the phosphinite groups are linked via 2 C atoms and which, together with the Rh atom, forms a 7-membered ring, Z is Cl, Br or I and A$\ominus$ is the anion of an oxygen acid or complex acid.

2. A process according to claim 1, wherein the reaction temperature is −20 to 50° C.

3. A process according to claim 1, wherein the hydrogen pressure is $4 \times 10^6$ Pa to $5 \times 10^7$ Pa.

4. A process according to claim 1, wherein X in the formulae III and IIIa is two ethylene groups or an open-chain or cyclic diene in which the diene groups are linked via 1 or 2 C atoms.

5. A process according to claim 4, wherein the diene is hexadiene, norbornadiene or cyclooctadiene.

6. A process according to claim 1, wherein Y in the formulae III and IIIa is a chiral diphosphine in which the phosphine groups are linked by 2 C atoms and which, together with the Rh atom, forms a 5-membered ring.

7. A process according to claim 1, wherein the phosphine groups contain $C_1$–$C_{12}$-alkyl, cycloalkyl which has 5 to 8 ring C atoms and can be substituted by 1 to 3 $C_1$–$C_6$-alkyl groups, phenyl, $C_7$–$C_{12}$-phenylalkyl or alkylphenylalkyl having 1 to 6 C atoms in the alkyl groups and 1 to 5 C atoms in the alkylene group.

8. A process according to claim 1, wherein A$\ominus$ is ClO$_4\ominus$, CF$_3$SO$_3\ominus$, BF$_4\ominus$, B(phenyl)$_4\ominus$, SbCl$_6\ominus$, AsF$_6\ominus$, or SbF$_6\ominus$.

9. A process according to claim 1, wherein the rhodium compound is added in an amount of 0.01 to 5 mol %, relative to the compound of the formula II.

10. A process according to claim 1, wherein, in formula III, X is cyclooctadiene, Z is Cl and Y is (R)— or (S)—

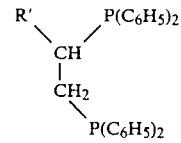

in which R' is methyl, phenyl or cyclohexyl.

11. A process according to claim 1, wherein, in formula II, R$^1$ is 2,6-dimethylphen-1-yl or 2-methyl-6-ethylphen-1-yl, R$^2$ is methyl and R$^3$ is methoxymethyl.

12. A process according to claim 1, wherein the diphosphinite is 1-0-phenyl-4-6-0-(R)-benzylidene-2,3-0-bis-(diphenyl-phosphino)-β-D-glucopyranoside.

* * * * *